United States Patent
Weiner et al.

(10) Patent No.: US 7,418,120 B2
(45) Date of Patent: Aug. 26, 2008

(54) METHOD AND SYSTEM FOR STRUCTURING DYNAMIC DATA

(75) Inventors: Allison Leigh Weiner, Milwaukee, WI (US); Saad A. Sirohey, Pewaukee, WI (US); Gopal B. Avinash, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 737 days.

(21) Appl. No.: 10/946,857

(22) Filed: Sep. 22, 2004

(65) Prior Publication Data
US 2006/0072797 A1 Apr. 6, 2006

(51) Int. Cl.
*G06K 9/00* (2006.01)
(52) U.S. Cl. .......................... 382/128; 382/203; 378/28
(58) Field of Classification Search ................ 382/100, 382/128, 129, 130, 131, 132, 133, 168, 173, 382/181, 184, 189, 203, 232, 256, 260, 270, 382/274, 276, 286, 305; 434/262; 600/300; 378/28
See application file for complete search history.

(56) References Cited

U.S. PATENT DOCUMENTS

| | | | | |
|---|---|---|---|---|
| 5,168,532 A | * | 12/1992 | Seppi et al. | 382/270 |
| 6,056,690 A | * | 5/2000 | Roberts | 600/300 |
| 6,366,683 B1 | * | 4/2002 | Langlotz | 382/128 |
| 6,669,482 B1 | * | 12/2003 | Shile | 434/262 |
| 6,785,410 B2 | | 8/2004 | Vining et al. | |
| 6,819,785 B1 | * | 11/2004 | Vining et al. | 382/128 |
| 7,289,651 B2 | * | 10/2007 | Vining et al. | 382/128 |

OTHER PUBLICATIONS

"Documenting the Information Content of Images," W. Dean Bidgood, Amer. Medical Informatics Ass'n Symposium 1997.
"Clinical importance of the DICOM structured reporting standard," W. Dean Bidgood, Int'l J. of Cardiac Imaging 14: 307-315, 1998.
"Image Acquisition Context: Procedure Description Attributes for Clinically Relevant Indexing and Selective Retrieval of Biomedical Images," W. Dean Bidgood et al., J. of the Amer. Medical Informatics Ass'n, vol. 6, No. 1, pp. 61-75, Jan./Feb. 1999.

* cited by examiner

*Primary Examiner*—Seyed Azarian
(74) *Attorney, Agent, or Firm*—McAndrews, Held & Malloy, Ltd.; Peter J. Vogel; Michael A. Dellapenna

(57) ABSTRACT

Certain embodiments of the present invention provide a system and method for structuring dynamic data from a plurality of images. Certain embodiments include accessing an image data set including data representing a plurality of images, determining a dynamic or functional attribute in the image data set, associating the dynamic or functional attribute with a lexical attribute from a lexicon, and storing the lexical attribute and an associated code. The lexical attribute and associated code may be stored in a database and/or a structured report, for example. The lexicon may be modified to accommodate attributes and medical terminology. Attributes relate to a feature and/or a region of interest in the image data set.

9 Claims, 10 Drawing Sheets

Timing of Image Data Sets

Over a Biological Cycle (or Portion)

At Specific Point in Cycle

Specified Time

Time Until an Event

Region

Finding (Stimuli)

User Selection

Image Data

Program Selection

Image Data

Image "No Flex"   Image "Flex"

Feature

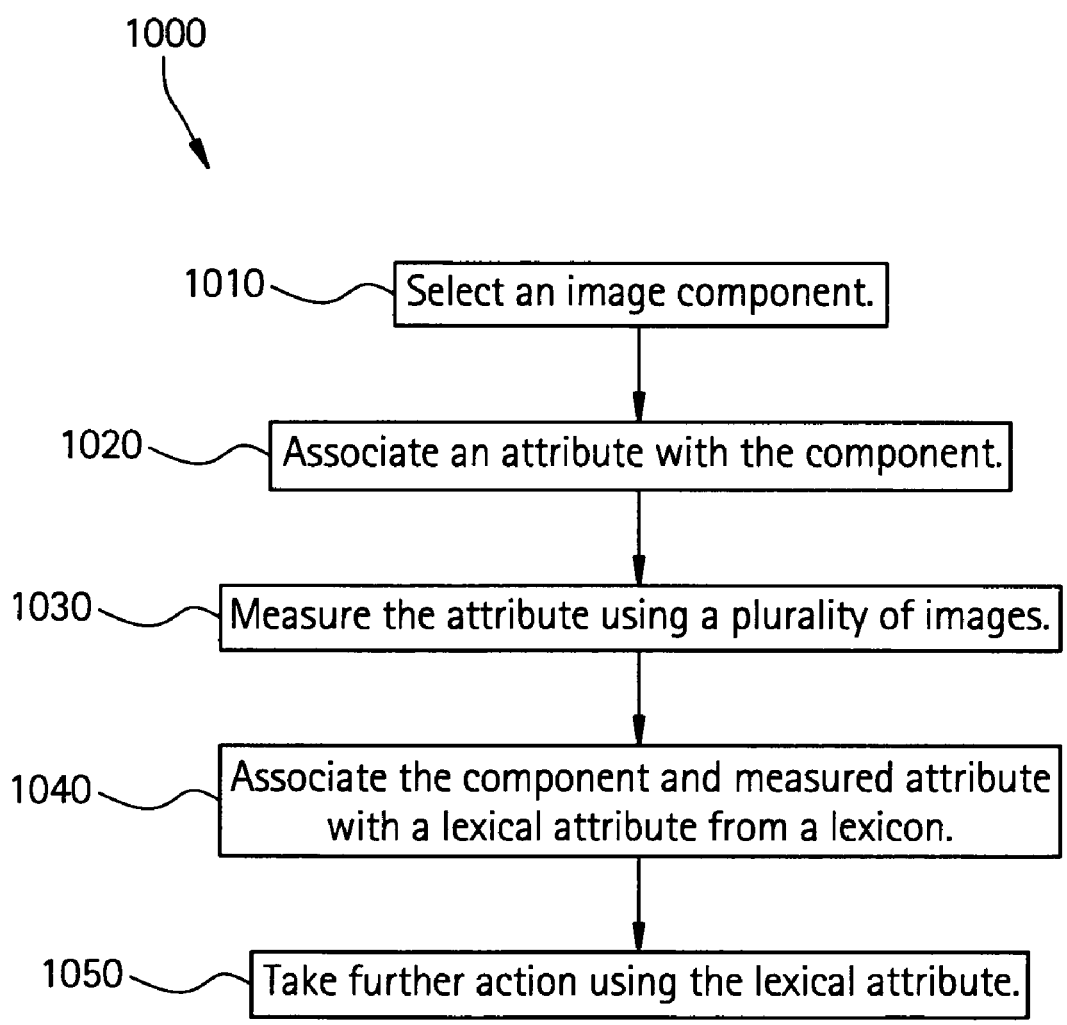

METHOD AND SYSTEM FOR STRUCTURING DYNAMIC DATA

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to structuring dynamic data. In particular, the present invention relates to a system and method for structuring dynamic data.

As the world becomes increasingly digital, medical technology also becomes increasingly digital. In prior systems, the output of a Radiology exam would be a series of films. Today, everything from routine X-rays and laboratory results to EKGs and complex MRI scans are available in electronic form and widely accessible through clinical and radiological information systems. Storing clinical data in a computer, particularly a computer situated on a network, creates an increasingly accessible clinical environment. However, merely storing data in electronic form does not overcome all problems associated with paper files. To locate a patient's exam, current systems still require knowledge of where the information is stored. Trying to locate a specific detail of an exam is even more difficult. Thus, a need exists to store clinical data in a form that is not only electronic, but accessible as well.

In radiology, every image taken during an exam may require a radiologist's examination. The radiologist views each image, marks down several findings and notes the findings in a report. The field of structured reporting emerged to organize radiologist reports in a manner that is easily accessible. A structured report for an exam consists of coded information. A radiologist associates findings with an image location and provides appropriate descriptions of findings based on the image coordinates and anatomical location. A report that stores references to the image or portions of the image with findings is generated. Additionally, the radiologist's findings may be coded. For example, the radiologist may pick a finding from a predefined list, with only certain findings allowed. This method has the added advantage of standardizing language, making it easier to find results. Computerization of structured report generation provides means for gaining productivity and ease of access to stored prior reports as well as a flexible user interface for the selection of the codified findings. These codified findings include finding descriptors anatomical location descriptors and position descriptors, for example. Using databases for storing such structured reports allows for ease of data mining, searches, etc.

Classical structured reporting works well as a tool to describe a single image representing static data, but fails to fully support applications requiring analysis of dynamic data. For example, in mammography, it is crucial to compare scans over time as opposed to in a single imaging session. It would be highly desirable to have an organized reporting system to systematically compare historical scans.

Additionally, it is often insufficient to examine a single image in a single imaging session. For example, when images are compared with biological cycles in response to external stimuli or other criteria, multiple images may be used for a radiologist to assess a situation. Many image or anatomy properties use multiple images for proper calculation. Functional properties of anatomical parts may be captured in a set of images over a select duration. Findings may be a result of certain attributes calculated over the select duration. Existing structured reporting systems do not include reporting for such information. Thus, current structured reporting systems do not accommodate recordation of dynamic or functional data obtained over multiple images. Therefore, a system for reporting dynamic data would be highly desirable.

Furthermore, current structured reporting systems restrict data entry to certain set formats for certain set types of information. As new formats become available, it would be highly desirable to have the ability to switch between different formats. Additionally, as new medical conditions or diagnostic data materialize it would be important to update the set formats to reflect changes. Thus, a flexible, dynamic structured reporting system would be highly desirable.

Therefore, there is a need for a system and method for structuring dynamic and functional data from a plurality of images and providing a flexible format to describe data.

BRIEF SUMMARY OF THE INVENTION

Certain embodiments of the present invention provide a system and method for structuring dynamic data from a plurality of images. Certain embodiments of a method include accessing an image data set including data representing a plurality of images, determining a dynamic attribute in the image data set, associating the dynamic attribute with a lexical attribute from a lexicon, and storing the lexical attribute and an associated code. The lexical attribute and associated code may be stored in a database and/or a structured report, for example. The lexicon may be modified to accommodate the dynamic attribute. The dynamic attribute relates to a feature and/or a region of interest in the image data set. The dynamic attribute may include a measurement relating to a feature and/or a region of interest over a plurality of images in the image data set. In an embodiment, a functional attribute may be determined in the image data set and associated with a lexical attribute.

Certain embodiments of an improved clinical data interface system include an attribute determination module for determining an attribute related to a component in an image data set, and a lexicon for associating the attribute with a lexical attribute. The image data set includes data representing a plurality of images. The attribute derived from the image data set.

In an embodiment, the lexicon may be modified and/or created to accommodate the attribute. The lexical attribute associated with the attribute may be stored in a database and/or a structured report. The system may also include a processing unit for processing the component, the attribute, and/or a measurement of the attribute. In an embodiment, the component includes a feature of the image data set and/or a region of interest in the image data set. The attribute may include a dynamic attribute and a functional attribute.

Certain embodiments of an improved lexicographic system for structuring attributes related to clinical findings include an attribute associated with a component of a clinical data set, and a lexicon customizable to accommodate the attribute. The lexicon may be modified and/or added to in substantially real time. The lexicon assigns a lexical attribute to the attribute. The clinical data set may be an image data set, an electrical data set, laboratory data, histological data, pharmacokinetic data, demographic data, and/or patient related data, for example.

The system may also include a data storage device including codes associated with the lexical attribute. The lexical attribute and the associated code assigned to the attribute are stored in a database and/or a structured report, for example. The attribute may be a dynamic attribute and/or a functional attribute.

Certain embodiments of a computer-readable storage medium include a set of instructions for a computer. The set of instructions includes an attribute determination routine determining an attribute related to a component in a clinical data set, wherein the image data set comprises data representing a plurality of images, where the attribute is derived from the clinical data set. The set of instructions also includes a lexicographic routine associating the attribute with a lexical attribute. In an embodiment, the lexicographic routine is modified to accommodate the attribute. The attribute may be a dynamic attribute and/or a functional attribute. The clinical data set may be an image data set, an electrical data set, laboratory data, histological data, pharmacokinetic data, demographic data, and patient related data, for example.

BRIEF DESCRIPTION OF SEVERAL VIEWS OF THE DRAWINGS

FIG. 10 illustrates a flow diagram for a method for image data analysis used in accordance with an embodiment of the present invention.

Figure 1:
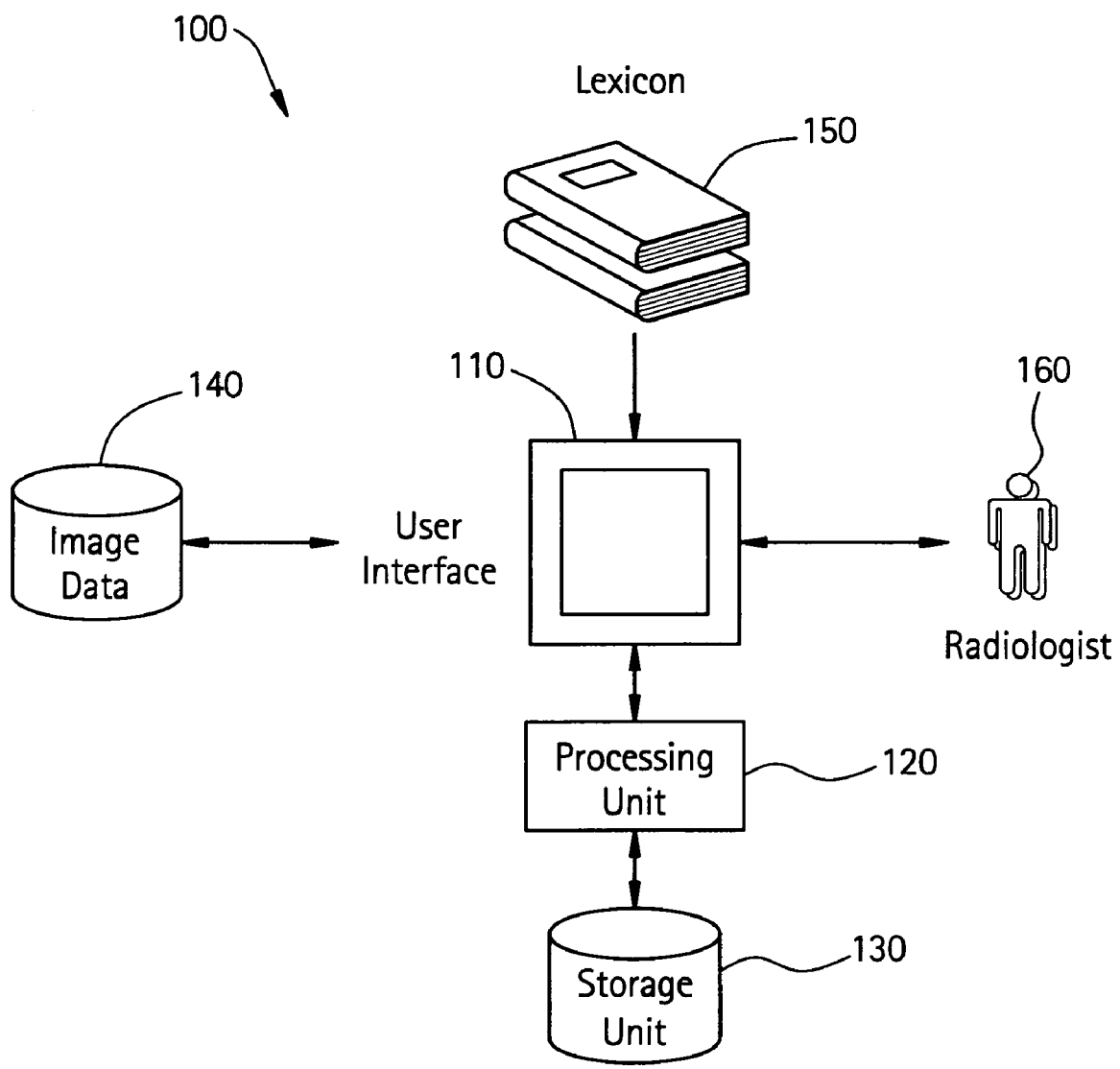
FIG. 1 illustrates an image data analysis and reporting system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an image data analysis and reporting system 100 used in accordance with an embodiment of the present invention. The system 100 includes a user interface 110, a processing unit 120, and a storage unit 130. The user interface 110 may receive input from and/or transmit output to a plurality of sources, such as image data 140, a lexicon 150, and a user 160 (for example, a radiologist). The units of the system 100 may be implemented in a single system, such as a computer or specialized processing system, or may be implemented in separate networked systems, for example. For example, the system 100 may be implemented in a Picture Archiving and Communication System (PACS), Clinical Information System (CIS), Radiology Information System (RIS), personal computer, or other computer system. The units may communicate via wired and/or wireless communication methods.

Figure 3:
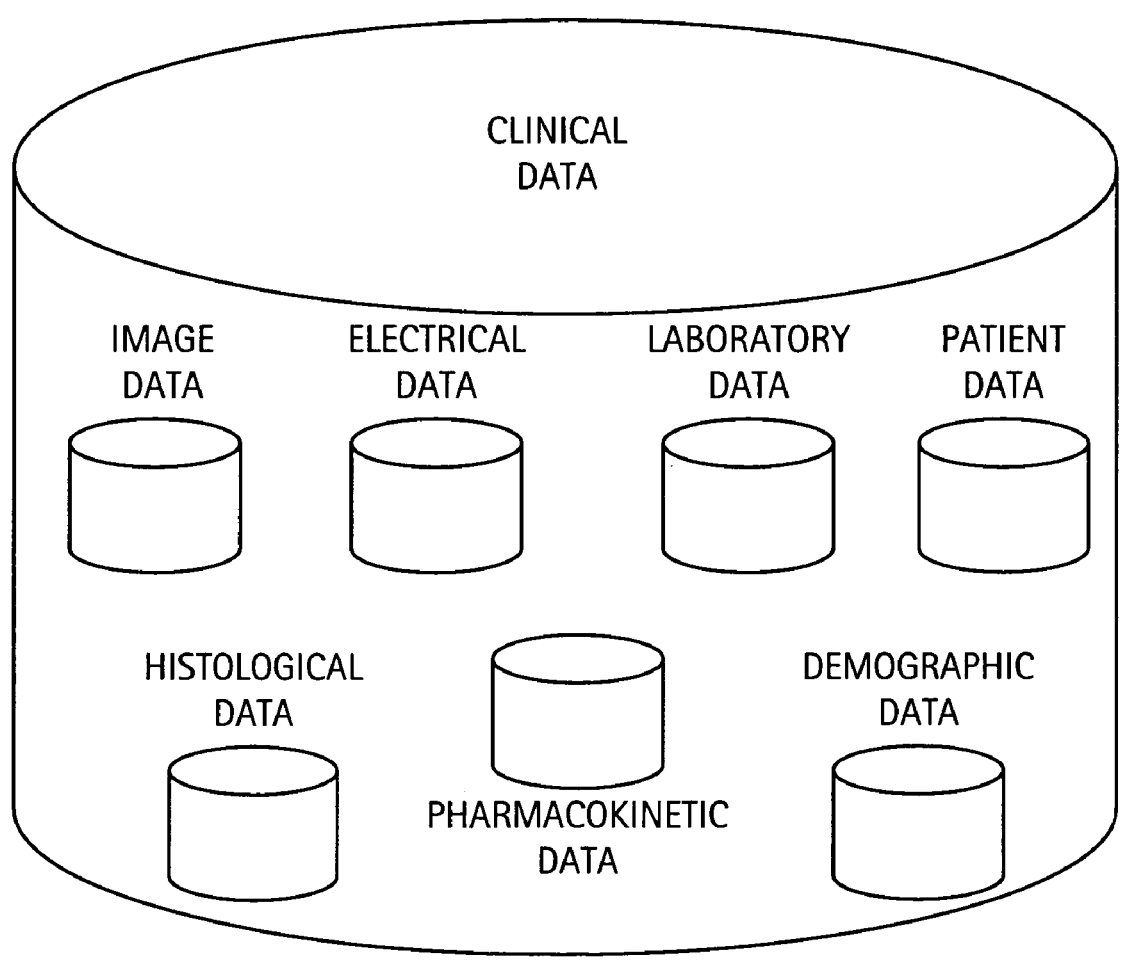
FIG. 3 depicts an example of clinical data used in accordance with an embodiment of the present invention.

Image data 140 includes data representing or more images of a subject, such as a patient anatomy, in conjunction with an imaging modality, such as x-ray, ultrasound, magnetic resonance, computed tomography, or other imaging mode. Image data 140 may be formatted for processing by the system 100. The image data 140 may be stored and/or routed to other components of the system 100 or external systems for processing and/or storage. In an embodiment, additional clinical findings, such as electrical data, laboratory data, histological data, pharmacokinetic data, demographic data, and patient related data, may also be acquired and stored, as shown in FIG. 3, for example.

The user interface 110 and/or processing unit 120 may be used to analyze image data 140 and/or other clinical and identify one or more image components (e.g., an image feature and/or region of interest) in an image set. As will be described further below, one or more image components may be identified manually, automatically, or with computer assistance via the processing unit 120. For example, a program running on a computer allows an operator 160 to highlight and/or select from a list a feature and/or region in an image.

The user interface 110 and/or processing unit 120 or attribute determination module may select one or more attributes related to the image component(s) selected. Attributes may be functional attributes (e.g., data representing a function of an organ, chemical data, or electrical data) and/or dynamic attributes (e.g., temporal data related to an anatomy). As will be described further below, one or more image attributes may be identified manually, automatically, or with computer assistance via the user interface 110 and/or processing unit 120. The user interface 110 and/or the processing unit 120 may be customized based on image data, user defined input, and/or protocol information, for example. For example, a program running on a computer allows an operator to enter and/or select one or more attributes related to image component(s) selected in an image set.

The processing unit 120 accepts image data 140. For selected attributes related to selected image components (e.g., feature(s) and/or region(s)), the processing unit 120 facilitates determination or acquisition of data relating to the attribute(s). Measurement data may be manually acquired, automatically determined, and/or determined by a user 160 with assistance from the processing unit 120 and/or user interface 110. The processing unit 120 may include or be connected to a processor, a probe, a meter, and/or other measurement system, for example, to determine quantitative and/or qualitative measurement for selected attributes with respect to selected image component(s). The processing unit 120 measures both static data and data of a dynamic nature (e.g., data that changes over time, data that tracks function of an anatomy or fluid, etc.). Measurement data may include image data, electrical data, laboratory data, histological data, pharmacokinetic data, demographic data, and/or patient related data, for example, as depicted in FIG. 3.

The processing unit 120 receives selected image component(s), one or more attributes selected for the image component(s), and measurements for the attributes. The processing unit 120 may store the data for future use and/or may execute action(s) using the data. Actions using the data may include generating a report such as a structured report (including storing and/or printing of the report), sending the data to another system or component, displaying the data, organizing the data, verifying accuracy of the data, querying the data, archiving or storing the data, analyzing the data using certain criteria, and/or performing administrative functions using the data, for example. The processing unit 120 may organize dynamic data, for example a combination of functional and temporal data, into a structured report.

The processing unit 120 includes a lexicon 150 for processing data in the system 100. The lexicon 150 is capable of processing static and/or dynamic data for functional and/or dynamic attributes from the image data 140, the user interface 110, and/or the processing unit 120, for example. The lexicon 150 generates lexical attributes which may be input in a report, such as a structured report.

In an embodiment, the lexicon 150 is a customizable lexicon. That is, the lexicon 150 includes a standard or default lexicon for the medical industry. If an attribute is not found in the standard lexicon, the lexicon 150 may be modified and/or updated to create a lexicon for the attribute(s). Additionally, a new lexicon may be created and saved in a data storage 130 associated with the processing unit 120. That is, lexical information may be stored in a database or other data store for use in creating reports or other representation of data. Lexical attributes may be associated with a set of codes, such as numeric or alphanumeric codes, for reporting or standardization purposes.

Figure 2:
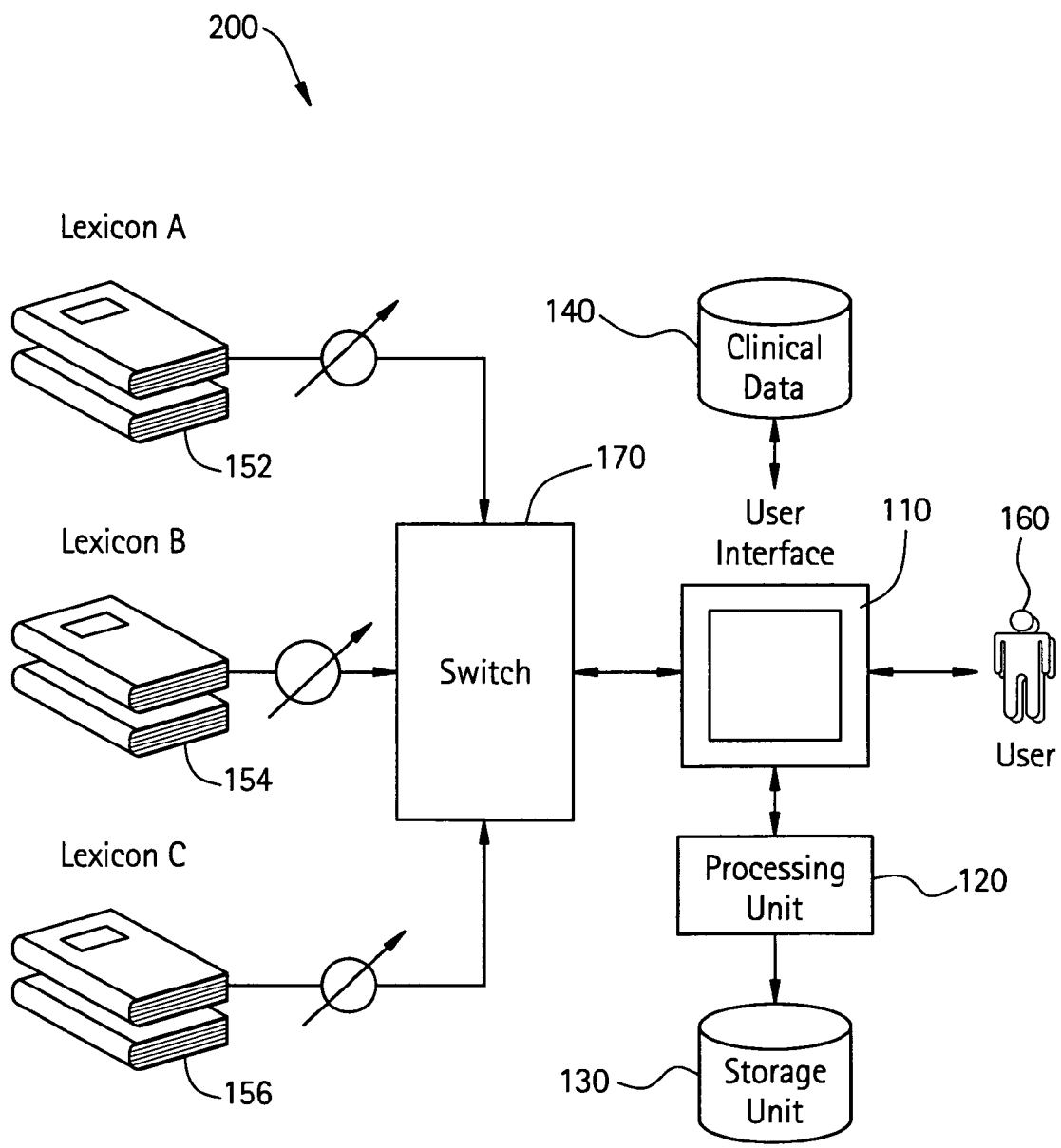
FIG. 2 illustrates an image data analysis and reporting system used in accordance with an embodiment of the present invention.

FIG. 2 illustrates an image data analysis and reporting system 200 used in accordance with an embodiment of the present invention. In the analysis and reporting system 200, a plurality of lexicons 152, 154, 156 are connected to the processing unit 120 through the user interface 110. A switch 170 allows the user interface 110 and/or the processing unit 120 to select a lexicon 152, 154, 156 for processing image and attribute data. Thus, a user 160 may select a lexicon 152, 154, 156 using the user interface 110 alone or in conjunction with the processing unit 120. Alternatively, the processing unit 120 may automatically select a lexicon 152, 154, 156 according to certain criteria. In an embodiment, multiple lexicons 152, 154, 156 may be selected to process data.

For example, the switch 170 allows the user interface 110 and/or processing unit 120 to select among a Digital Imaging and Communications in Medicine (DICOM) Structured Reporting standard lexicon, a Health Level 7 (HL 7) standard lexicon, and/or a new lexicon. Selected lexicon(s) may be customized via the user interface 110 and/or processing unit 120.

Thus, dynamic attributes and functional attributes may be associated with a dynamic lexicon for storage and reporting. Structure may be applied to dynamic data to increase uniformity and usability of the dynamic data. Processing systems and/or other medical systems (such as prescription systems, clinical management systems, PACS systems, etc.) may use the lexical attribute information and/or lexical codes for diagnosis, treatment, and/or clinical study, for example. For example, lexical attributes may be formatted in a report so that a physician or other medical personnel may use the data for treatment without having to repeat data selection, measurement, and processing.

A lexicon and lexical attributes may be provided in a pull-down menu or other list or user interface, for example, to provide a simple, efficient interface for medical personnel. A template may be loaded on the system 100 and modified by software and/or a user. The template may include an electronic medical record, a structured report, a data summary, a picture, and/or other data representation.

Figure 4:
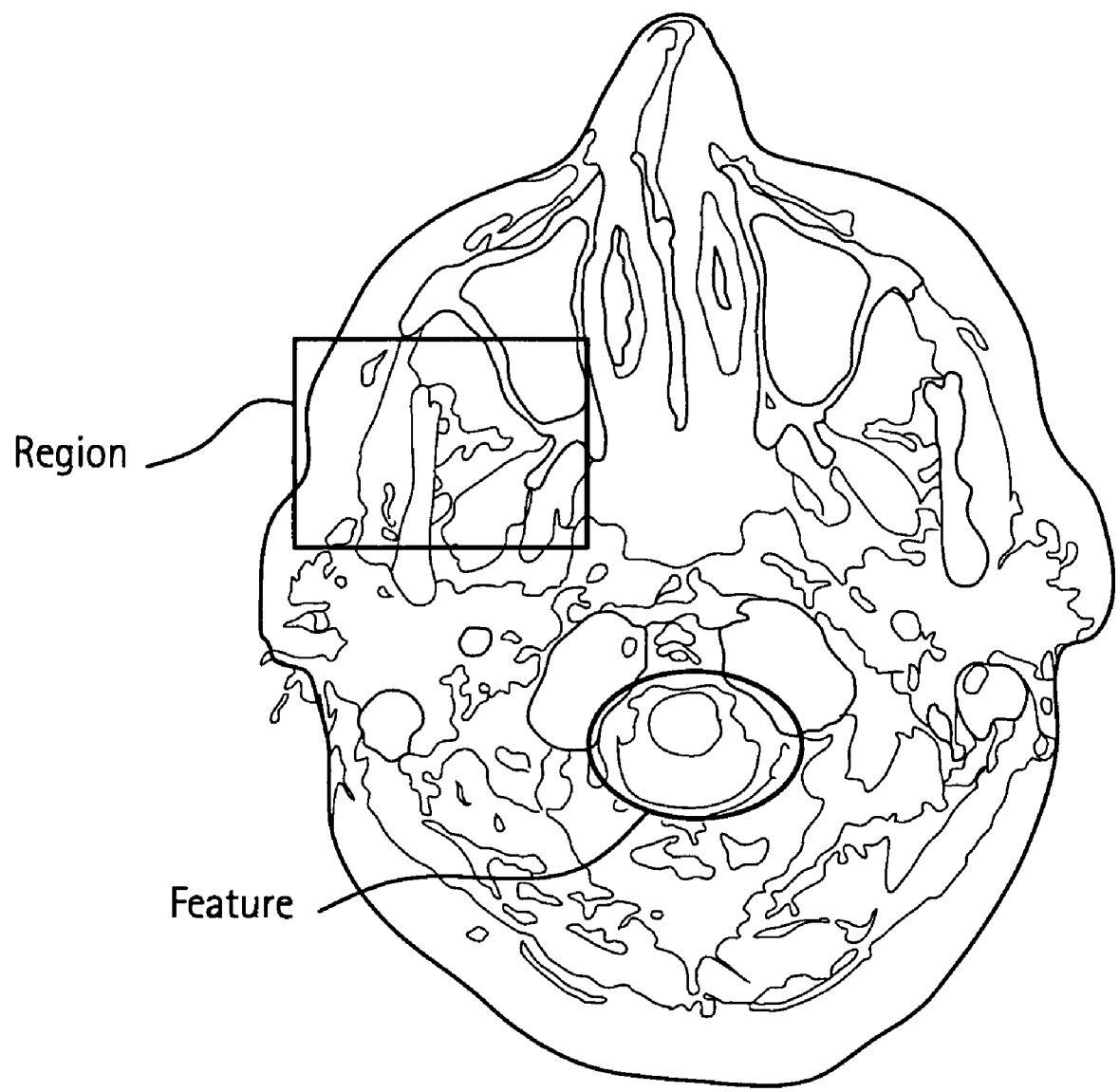
FIG. 4 depicts an image highlighting an example of a feature and a region in a brain slice image.

Image data analysis may be conducting using an image component, such as a feature and/or a region of interest, in one or more images. FIG. 4 depicts an image highlighting an example of a feature and a region in a brain slice image. A region is indicated by a box in FIG. 4. A feature may be indicated by the corpus collosum, for example, circled in FIG. 4.

Figure 5A:
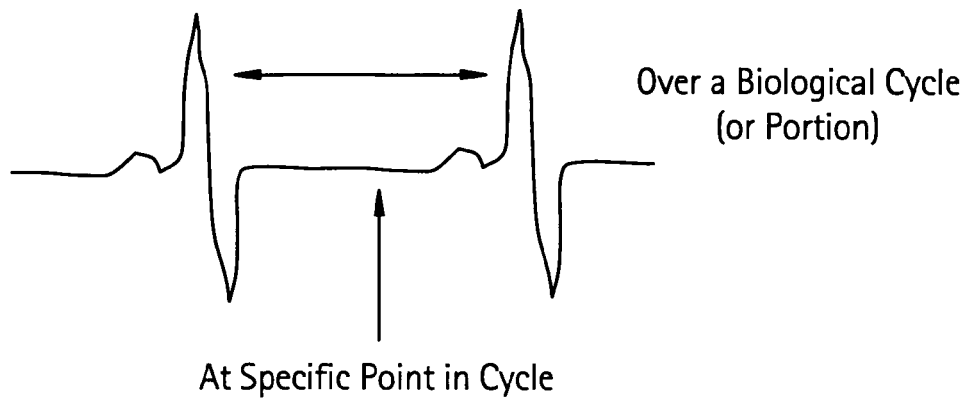
FIG. 5 illustrates examples of timing of image data sets in accordance with an embodiment of the present invention.
Figure 5B:
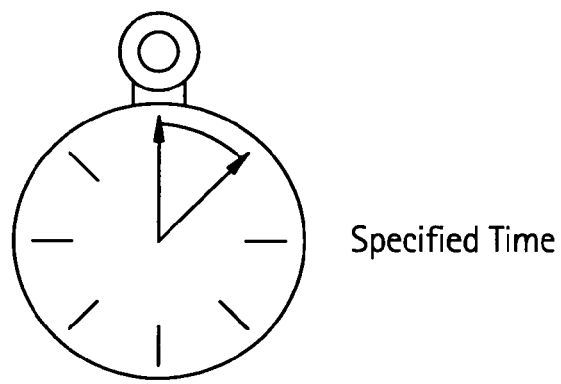
Figure 5C:
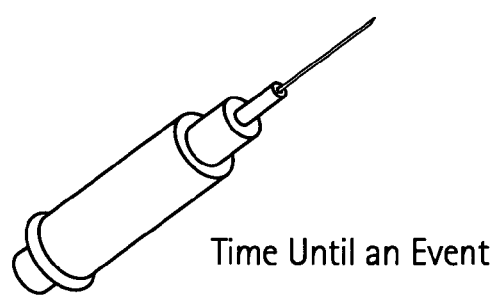
Figure 6:
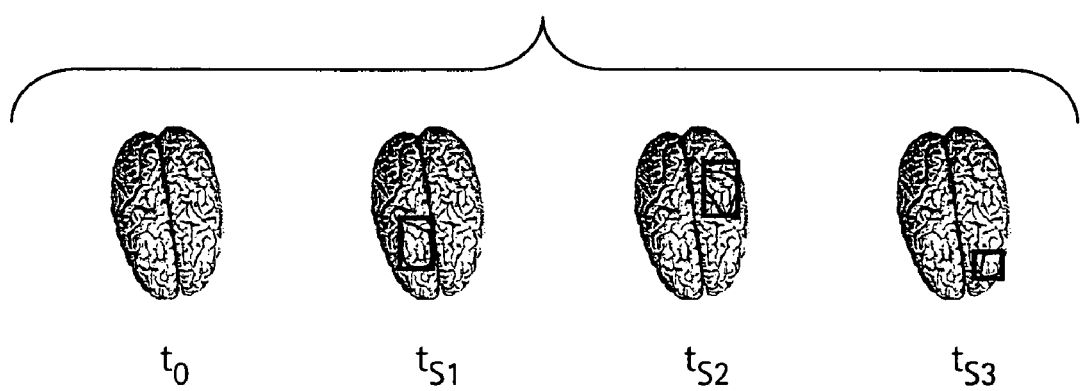
FIG. 6 shows image data acquisition at certain times in response to certain stimuli in certain region of a brain scan in accordance with an embodiment of the present invention.
Figure 6:
Figure 6:

Image data may represent images acquired in one or more imaging sessions. Images may have been acquired over a portion of a biological cycle, a specific part of biological cycle, some arbitrary time (e.g., temporal data), in response to an event (e.g., absorption of contrast, response to an external stimulus, etc.), or determining functional behavior. FIG. 5 illustrates examples of timing of image data sets in accordance with an embodiment of the present invention. FIG. 5(a) illustrates image data acquisition at a specific point in a biological cycle or portion of a biological cycle. FIG. 5(b) shows image data acquisition at a specific point in time. FIG. 5(c) depicts image data acquisition in response to a particular event, such as absorption of a contrast agent. FIG. 6 shows image data acquisition at certain times ($t_0$-$ts_3$) in response to certain stimuli in certain region of a brain scan.

In operation, image data may come from a variety of sources. Images may have been generated from one or more imaging sessions, involve different modalities (e.g., ultrasound, magnetic resonance, computed tomography, x-ray, positron emission tomography, nuclear, thermal, optical, video, etc.), views, slices, and/or protocols. Images may have originated from a single source or be a result of calculation (e.g., fused or compound images from multiple modalities).

The region or feature of interest may be selected in a single image, some images of a group, or all images to be analyzed. Additionally, selections may be made using a model, atlas, or fused image data (e.g., image data from multiple image data sets that are registered and combined to form a single image), for example. The feature or region may be any size or shape. Position, size, and shape of the region or feature under investigation may vary across images. Segmentation, registration, and/or pattern matching may provide correspondence between position, size, and/or shape of the region or feature across images.

Figure 7A:
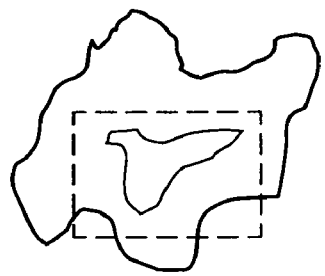
FIG. 7 depicts examples of selection of a feature or region of interest in an image according to an embodiment of the present invention.
Figure 7A:
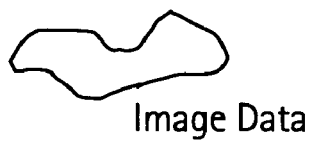
Figure 7B:
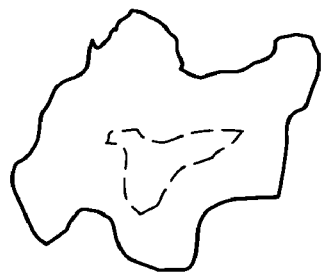
Figure 7B:
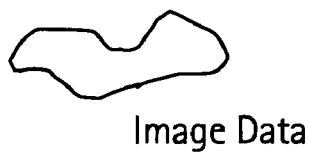

The region or feature of interest may be selected using a variety of methods. The region or feature may be manually selected. For example, a user inputs coordinates on an image or "draws" on the image using an input device, such as a mouse, touchpad, or trackball. FIG. 7(a) depicts an example of user selection of a region or feature of interest in an image using an input device, such as a mouse. The region or feature may also be selected by a user with an aid, such as computer adjustment. For example, as shown in FIG. 7(b), a user inputs coordinates or draws on the image, and software modifies the user selection to fit a region or feature. Additionally, the region or feature may be selected using a menu. For example, a user uses a menu to input which feature or region to use (e.g., Nodule A, Coronary Artery, or Upper Left Quadrant). The region or feature may also be selected automatically. For example, features and/or regions may be detected and selected automatically using a computer system.

Figure 8A:
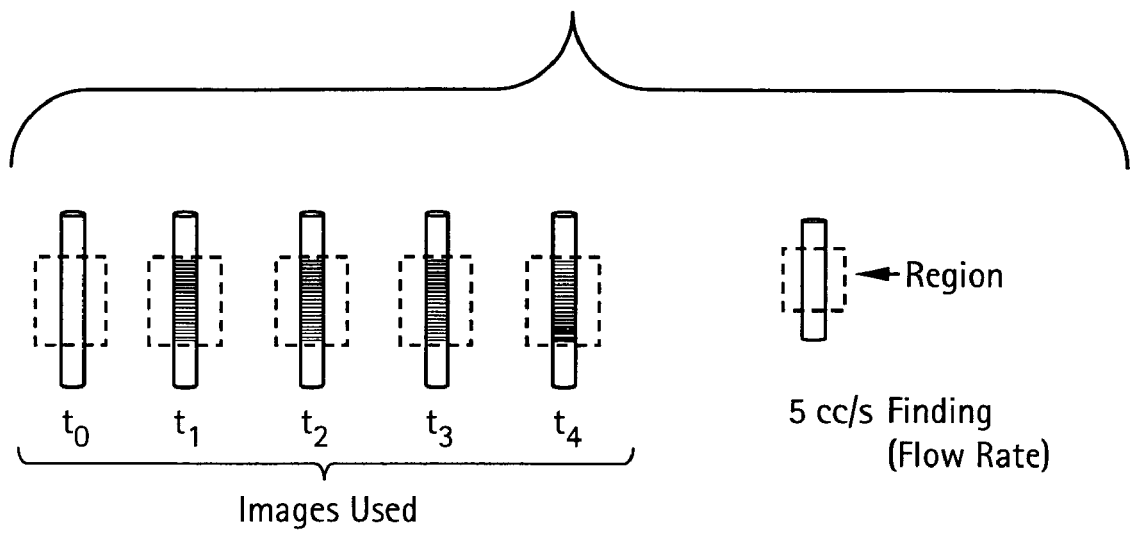
FIG. 8 shows example of property types used in accordance with an embodiment of the present invention.

A variety of attributes may be associated with a feature and/or region. For example, an attribute may be time-based, path-based, and/or mechanical, for example. A time-based attribute is an attribute that is calculated over a specified time. FIG. 8(a) shows an example of determining flow rate based on contrast in an image. The dotted square represents an area of interest. Time t0 represents the region without contrast. As time progresses ($t_1$-$t_4$), contrast flows in and out of the region, represented by a lightening or darkening of the region. Flow rate may be determined by comparing a pixel intensity of time compared to the $t_0$ image. As illustrated in FIG. 3, attributes may include clinical data, such as image data, an electrical data, laboratory or experimental data, histological data, pharmacokinetic data, demographic data, and patient related data, for example.

Figure 8B:
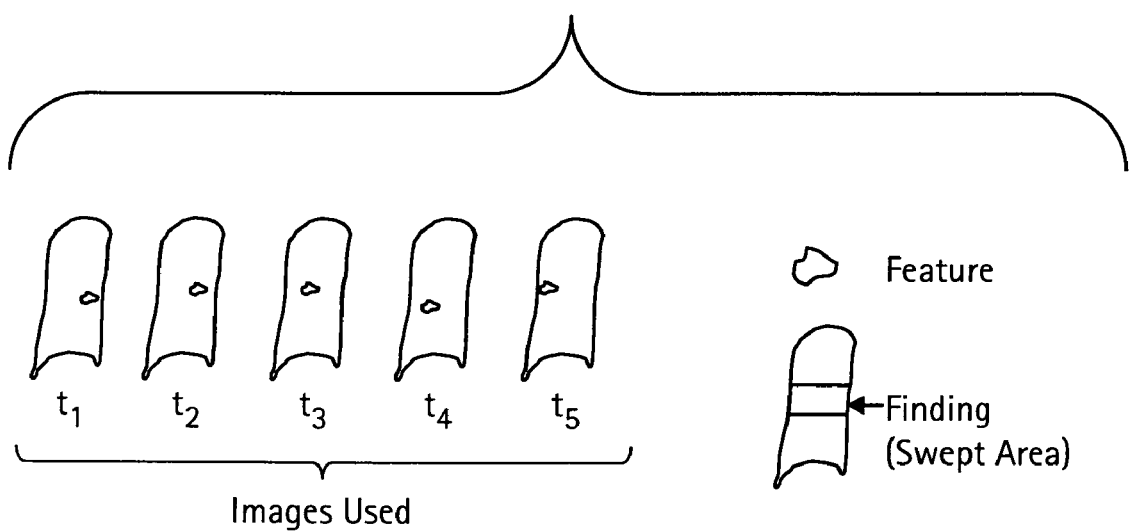

A path-based attribute is a physical attribute that is calculated over a set of images. FIG. 8(b) shows an example of determining variation in position of a nodule over time for treatment planning. The feature (e.g., a nodule) is followed through multiple images throughout a biological cycle. The finding represents an area swept by the nodule and may be used to determine an area of irradiation for radiation therapy, for example.

Figure 9:
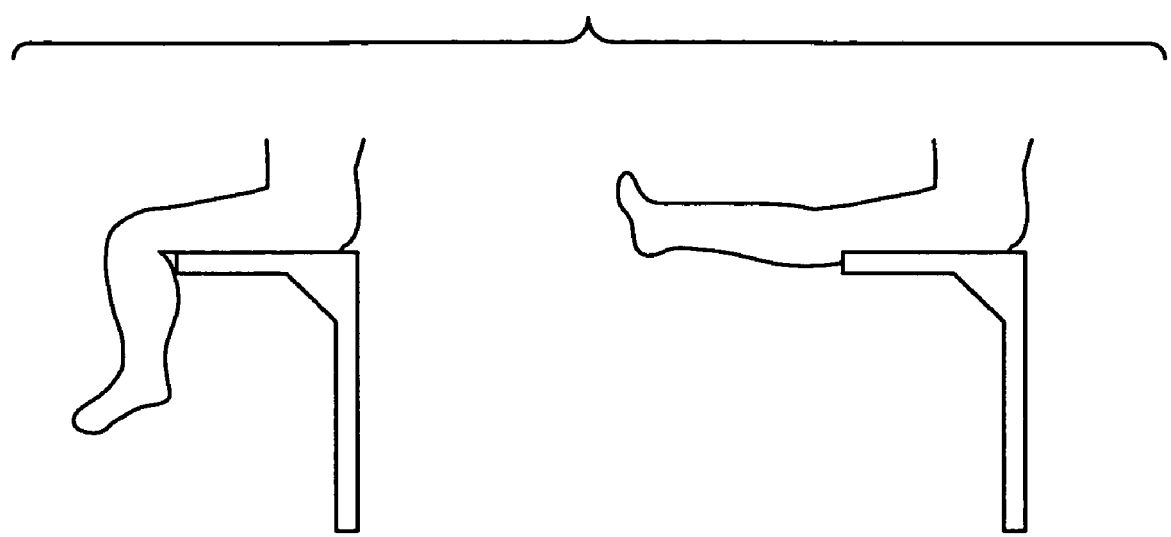
FIG. 9 depicts an example of determining a degree of flexion in a knee in accordance with an embodiment of the present invention.
Figure 9:
Figure 9:
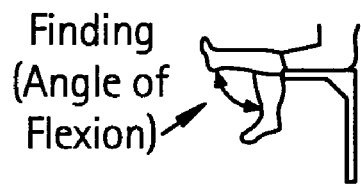

A mechanical attribute is an attribute that represents a mechanical aspect, such as force, range of motion, stress, or strain. FIG. 9 depicts an example of determining a degree of flexion in a knee. A first "No Flex" image shows the knee without flexion. A second "Flex" image shows the knee in a flexed position. The degree of flexion may be determined by comparing the two images. Similar techniques may be used to compare the degree of flexion over time.

Attributes may be selected using a variety of methods. An attribute may be selected using manual input. For example, a user types or otherwise enters the attribute to be determined. An attribute may also be selected using a menu. For example, a user selects the attribute from a menu. The menu may include all attributes in a program or may represent a list of possible attributes (e.g., attributes specific to a particular image data, patient, or study). An attribute may also be selected automatically. For example, selection of one or more attributes is automatically determined. The determination may be based on user preferences, protocols, or a feature/region selected, for example.

Attribute measurement may be determined by a variety of methods. Attributes may be manually measured. That is, a user measures an attribute without computer aid. Attributes may be measured using a computer. For example, a user measures an attribute using computerized tools (e.g., rulers, annotations, etc.). Attributes may also be measured automatically by computer. For example, an attribute measurement may be automatically determined without user intervention. Attributes may be measured over time and/or over a series of images to determine a change in data, for example.

In order to measure an attribute in images acquired at different times, multiple images may be registered (i.e., points in multiple images correlated against a reference coordinate system) to enable measurement across images. Additionally, images may be stretched, shrunk, or otherwise processed, in whole or in part, to match regions or features of interest. For example, if a lung nodule is being measured over a breathing cycle, the nodule moves over time. Thus, the nodule is "found" or segmented in each image used in order to compare attributes of the nodule over time.

Once an attribute has been measured for a feature or region, the measurement may be used in a variety of ways. Information, such as attribute measurement and/or image component (feature/region) data, may be organized in a variety of ways. For example, information may be organized based on patient, protocol information, user, and/or pre-defined template. Information may be organized in a report according to the above criteria.

Information may also be verified. For example, a radiologist may verify the attribute/image component information by displaying a representation or a report of the information. Information may also be displayed in raw form, report form, and/or image representation to a user.

Information may be archived in raw and/or report form in a storage device, such as a computer database. Information storage may be permanent or temporary. Information may be sent in raw and/or report form to another location. For example, information may be transmitted via physical transport or electronic system (Web, email, local area network, wide area network, satellite, etc.). Information may be sent to a clinician, radiologist, specialist, administrator, research institution, or other location, for example.

Information may be further processed or utilized. Information may be used to query a database or registry, for example, to identify similar information or report. Information may be used with a diagnostic database to determine information about a patient's condition, for example.

As mentioned above, information regarding a feature and/or region and associated attributes may be organized in a report. Supporting data may also be included in the report. The report may be organized in a variety of ways, such as based on patient, protocol information, user, and/or pre-defined template. The report may be stored in computer memory, for example, for further reference.

A lexicon may be used to place report data in a standardized form. As discussed above, the lexicon may be modified and/or created as needed. That is, if an attribute is found in the existing lexicon, the corresponding lexical attribute and associated code may be used. If the attribute is not found in the existing lexicon, a corresponding lexical attribute and associated code may be added to the lexicon. If a lexical attribute is deficient, the lexicon may be modified. The ability to modify a lexicon may be restricted to certain users of the system. Medical communication standards and lexicons, such as Health Level 7 (HL7) standard, Systematized Nomenclature of Human and Veterinary Medicine (SNOMED) glossary, Digital Imaging and Communications in Medicine (DICOM) Structured Reporting standard, American College of Radiology (ACR) Index of Radiological Diagnoses, American National Standards Institute (ANSI) reporting standard, Logical Observation Identifier Names and Codes (LOINC) database, and other vocabularies, for example, may provide a basis for assigning codes to attributes.

The report may include feature/region attribute information such as position(s) in an image, anatomical position(s), text description, and/or snapshot of the feature/region, for example. If a snapshot is present in a report, the snapshot may include a single static or morphed image or multiple static or cine images.

The report may include attribute information including attribute measurement and/or attribute description. Attribute measurement may include numerical measurement, characterization of an attribute measurement, and/or a measurement data set, for example. Attribute description may include analysis and/or conclusions involving the attribute information.

The report may also include supporting data related to the image component and attribute information or patient condition and disposition. The supporting data may include patient information, procedure information, radiologist information, diagnosis information, treatment information, referral information, additional reports, priority information, and/or billing information, for example. Patient information may include patient characteristics (e.g., gender, age, etc.), patient history, and/or visit-specific information, for example. Procedure information may include operator information and/or data acquisition context, such as modality, protocol, and/or series information, for example. Additional report(s) may be related to imaging and/or may be unrelated to imaging information. Additional report(s) may be historical reports or reports related to a particular clinical visit. Additional report (s) may include information relating to patients similar to the current patient. Priority information in a report may be administrative-related information and/or health-related information (e.g., critical, watch, unimportant, etc.).

FIG. 10 illustrates a flow diagram for a method 1000 for image data analysis used in accordance with an embodiment of the present invention. First, at step 1010, an image component is selected. That is, an identifiable feature or structure, such as a nodule, artery, organ, or other structure, is selected in an image. Alternatively, a region of interest in the image may be selected. That is, an arbitrary region, such as a cranial or chest cavity, or subset is selected in an image. In an embodiment, multiple components (i.e., features and/or regions of interest) may be selected for comparison between images.

Then, at step 1020, one or more attributes are associated with the component. For example, attributes for the selected component are identified in a list. Next, at step 1030, the one or more attributes are measured using two or more images. For example, image(s) are examined to measure and/or extract data for the identified attributes related to the selected component.

For example, a region in an image may be selected to measure contrast in the region. The brightness of the region may be selected in any image. Brightness may be measured in multiple images. Additionally, time between image acquisitions is recorded, and differences in brightness levels between images are determined. Thus, the dynamic rate of contrast flow in a region may be measured.

At step 1040, further action may be taken using the measured data and other image information. Actions taken using the data may include generating a report (for example, a structured report), sending the data to another system or component (for example, to a storage system, a medical practitioner, and/or a processing system), displaying the data (for example, in printed form and/or on a television, LCD, or other display), organizing the data (for example, based on patient, protocol information, user information, and/or template), verifying accuracy of the data (for example, through verification by a radiologist or other practitioner and/or through verification by comparison to another data set), querying the data (for example, identifying certain data or using data to locate similar data and/or reports in another data source), archiving or storing the data (for example, in a computer database, PACS, HIS/RIS, RAID system, application service provider, or other data store), analyzing the data using certain criteria (for example, a diagnostic, treatment, or other reference database), and/or performing administrative functions (for example, using the data to initiate an administrative workflow or other workflow), for example. As described above, a customizable lexicon may be used to associate functional and/or dynamic attributes and related data with standardized lexical attributes and codes for more uniform processing and reporting of medical data.

For example, for blood perfusion, a lexicon may define certain lexical attributes such as input volume, output volume, threshold (e.g., greater than, less than, etc.), mean blood flow, and/or stratification (e.g., high or low ejection fraction ratio). Thus, certain values may be linked to lexical attributes. The lexicon may be updated in the future as additional data is obtained.

As another example, for brain activation, a lexicon may define lexical attributes such as anatomy descriptors (e.g., location, description, etc.), dynamic measurements (e.g., volume, areas, number, percentage of normal reference, etc.), and/or dynamic descriptors (e.g., improvements to non-infarcted hemispheres, enlargement of activation foci, etc.).

In another example, for three-dimensional anatomical position over a cycle, a lexicon may define lexical attributes such as anatomical data, anatomy type (e.g., segmented structure, composite structure, system, region, part of superstructure, has substructures, part of physiological system, part of body system, etc.), and/or anatomy name. Thus, for example, a respiratory cycle may be imaged and measured in a three-dimensional volume over time. The cycle may be stratified for diagnosis and/or treatment purposes.

Dynamic data may be structured using a lexicon that defines lexical attributes such as shape changes, volume of interest (VOI), VOI boundaries, start position, end position, and/or percentage of critical organ clearance during respiratory cycle (e.g., VOI is clear of critical organs for all of a cycle, VOI is clear of critical organs for 50% of a cycle, or VOI is not clear of critical organs). Lexical attributes allow dynamic data obtained over multiple images to be structured and stored with other data for use in treatment, diagnosis, electronic medical records, structured reports, and other data storage, for example.

Thus, certain embodiments provide structured reporting of dynamic image findings. Certain embodiments provide increased efficiency and diagnostic ability for radiologists and other medical practitioners composing and reviewing images and associated reports. In addition, by standardizing findings and both functional and dynamic attributes used in reports, data mining applications, such as computer-aided diagnostics, are easier to execute.

Certain embodiments address findings found in multiple images, rather than just a single image. Comparing multiple images allows calculations of numerous properties, such as flow, range of motion, response to stimuli, and other properties, which have a wide variety of clinical value. Certain embodiments allow structuring of dynamic data which changes or develops over time. Thus, both static and dynamic data may be used and shared in a structured form.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An improved method for interfacing with clinical data across multiple images, said method comprising:
    accessing an image data set, wherein said image data set comprises data representing a plurality of images;
    determining a dynamic attribute in said image data set, said dynamic attribute measured with respect to said plurality of images and changing over time among said image data set;
    associating said dynamic attribute with a first lexical attribute from a lexicon;

determining a functional attribute in said image data set;

associating said functional attribute with a second lexical attribute; and storing said first and second lexical attributes and associated codes in conjunction with said image data set of said plurality of images.

2. The method of claim 1, wherein first and second lexical attributes and said associated codes are stored in at least one of a database and a structured report.

3. The method of claim 1, wherein said lexicon is modified to accommodate said dynamic attribute.

4. The method of claim 1, wherein said dynamic attribute relates to at least one of a feature and a region of interest in said image data set.

5. The method of claim 1, wherein said dynamic attribute further comprises a measurement related to at least one of a feature and a region over a plurality of images in said image data set.

6. An improved lexicographic system for structuring attributes related to clinical findings, said system comprising:

a dynamic attribute associated with a component of a clinical data set, said clinical data set spanning a plurality of images, said dynamic attribute measured with respect to said plurality of images and changing over time in conjunction with said clinical data set;

a functional determined from said clinical data set;

a lexicon customizable to accommodate said dynamic attribute, and said functional attribute, said lexicon capable of being at least one of modified and added to in substantially real time, said lexicon assigning a lexical attribute to said dynamic attribute and to said functional attribute.

7. The system of claim 6, wherein said clinical data set comprises at least one of an image data set, an electrical data set, laboratory data, histological data, pharmacokinetic data, demographic data and patient related data.

8. The system of claim 6, further comprising a data storage device including codes associated with said lexical attribute.

9. The system of claim 8, wherein said lexical attribute and said associated code assigned to said dynamic attribute and said functional attribute are stored in at least one of a database and a structured report.

* * * * *